US005549901A

United States Patent [19]
Wright

[11] Patent Number: 5,549,901
[45] Date of Patent: Aug. 27, 1996

[54] ANTIMICROBIAL OIL-IN-WATER EMULSIONS

[75] Inventor: D. Craig Wright, Gaithersburg, Md.

[73] Assignee: Novavax, Inc., Rockville, Md.

[21] Appl. No.: 322,827

[22] Filed: Oct. 13, 1994

Related U.S. Application Data

[63] Continuation-in-part of Ser. No. 246,868, May 20, 1994.
[51] Int. Cl.$^6$ ...................................................... A61K 7/40
[52] U.S. Cl. ............................................................ 424/401
[58] Field of Search ................................................ 424/401

[56] References Cited

U.S. PATENT DOCUMENTS

| | | | |
|---|---|---|---|
| 4,902,720 | 2/1990 | Baldone | 514/642 |
| 5,039,688 | 8/1991 | Lewis | 514/538 |

OTHER PUBLICATIONS

*McCutcheon's Detergents & Emulsifers 1971 Annual,* (New Jersey: Allured Publishing Company 1971), pp. 49,86.
*Remington's Pharmaceutical Sciences* (1985), 17th Edition: pp. 317–318, 328.

Isaacson, P. G., "Gastric Lymphoma and *Helicobacter Pylori*" *New England Journal of Medicine*, vol. 330, No. 18, pp. 1310–1311, 5 May 1994.

Parsonnet, J. et al., "*Helicobacter Pylori* Infection and Gastric Lymphoma" *New England Journal of Medicine*, vol. 330, No. 18, pp. 1267–1271, 5 May 1994.

*Primary Examiner*—Marianne M. Cintins
*Assistant Examiner*—Keith MacMillan
*Attorney, Agent, or Firm*—Lahive & Cockfield

[57] ABSTRACT

An antimicrobial lipid-containing oil-in-water emulsion comprising an agent selected from the group consisting of glycerol monooleate, glycerol trioleate, glycerol monolaurate, and glycerol dilaurate as the primary lipid and a cationic halogen-containing compound having a $C_{12}$–$C_{16}$ chain as a positive charge producing agent is disclosed. The antimicrobial emulsion can be used in the form of a pharmaceutical preparation to inhibit the growth of a wide variety of infectious pathogens.

11 Claims, No Drawings

ANTIMICROBIAL OIL-IN-WATER EMULSIONS

RELATED APPLICATIONS

This application is a Continuation-In-Part application of U.S. Ser. No. 08/246,868, filed May 20, 1994, the contents of which are incorporated herein by reference.

BACKGROUND OF THE INVENTION

The present invention relates to an antimicrobial lipid-containing oil-in-water emulsion which inactivates infectious pathogens upon contact.

It is known that if a water-immiscible liquid phase is mixed into an aqueous phase by mechanical agitation, for example, by means of an ultra-disperser, the stability of the resulting oil-in-water dispersion most frequently requires the addition of an emulsifying agent, the molecules of which are adsorbed onto the surface of the oil droplets to form a kind of continuous membrane which prevents direct contact between two adjacent droplets. The drops of oil can further contain substances soluble in an organic medium, such as a sterol.

In addition to discrete oil droplets dispersed in an aqueous phase, oil-in-water emulsions can also contain other lipid structures, such as small lipid vesicles (i.e., lipid spheres which often consist of several substantially concentric lipid bilayers separated from each other by layers of aqueous phase), micelles (i.e., amphiphile molecules in small clusters of 50–200 molecules arranged so that the polar head groups face outward toward the aqueous phase and the apolar tails are sequestered inward away from the aqueous phase), or lamellar phases (lipid dispersions in which each particle consists of parallel amphiphile bilayers separated by thin films of water). These lipid structures are formed as a result of hydrophobic forces which drive apolar residues (i.e., long hydrocarbon chains) away from water.

The portals of entry of pathogenic bacteria, viruses or fungi are predominantly the skin and mucus membranes, and upper and lower respiratory tracts. The first step in any infection is attachment or colonization on skin or mucus membranes with subsequent invasion and dissemination of the infectious pathogen. Accordingly, an object of the present invention is to provide an antimicrobial emulsion which inactivates infectious pathogens on contact by disrupting their membrane structures.

SUMMARY OF THE INVENTION

The present invention provides a stable antimicrobial oil-in-water emulsion for inactivating infectious pathogens upon contact. The emulsion comprises positively charged droplets of a lipid-containing oily "discontinuous phase" dispersed in an aqueous "continuous phase". The discontinuous phase of the emulsion of the present invention appears to bind to the biological membrane of a pathogen and subsequently solubilizes the membrane. The emulsion has microbicidal activity against a broad spectrum of bacteria, viruses and yeasts.

The antimicrobial emulsion of the present invention consists primarily of positively charged droplets of a lipid-containing oily discontinuous phase dispersed in an aqueous continuous phase, such as water. The discontinuous phase contains an amphiphile selected from the group consisting of glycerol monooleate (GMO), glycerol trioleate (GTO), glycerol monolaurate (GML), and glycerol dilaurate (GDL) as the primary lipid and a cationic halogen-containing compound having a $C_{12}$–$C_{16}$ chain as a positive charge producing agent. The droplets can further contain a sterol, such as cholesterol or phytosterol. The droplets appear to bind to negatively charged proteins contained in bacterial, viral, or fungal membranes, thereby disrupting the membrane structure and irradiating the pathogen.

Antimicrobial emulsions of the present invention are non-toxic and safe, for example, when swallowed, inhaled, or applied to the skin. This result is unexpected since many cationic halogen-containing compounds having a $C_{12}$–$C_{16}$ chain are extremely toxic if administered alone. For example, cetylpyridinium chloride (CPC), a preferred cationic halogen-containing compound of the invention, causes severe irritation and damage to tissues of the upper respiratory tract, mucous membranes and skin. However, when administered in the form of an emulsion of the invention, no such adverse effects occur. Furthermore, the emulsions of the invention are stable when heated or exposed to significant levels of acid and base.

The positive charge of the oily discontinuous phase is provided by a cationic halogen-containing compound having a $C_{12-C16}$ chain. In a preferred embodiment, the cationic halogen-containing compound having a $C_{12}$–$C_{16}$ chain is selected from the group consisting of cetylpyridinium chloride (CPC), cetypridinium bromide (CPB), and cetyltrimethylammonium bromide (CTAB). Other cationic halogen-containing compounds having a $C_{12}$–$C_{16}$ chain which can be used include, for example, cetyltrimethylammonium chloride, cetyldimethylethylammonium bromide, cetylbenzyldimethylammonium chloride, cetyltributylphosphonium bromide, dodecyltrimethylammonium bromide, and tetradecyltrimethylammonium bromide.

The oily discontinuous phase can further contain at least one sterol selected from the group consisting of cholesterol, cholesterol derivatives, hydrocortisone, phytosterol, and mixtures thereof. The term "cholesterol derivatives," as used herein, includes but is not limited to sulfate and phosphate derivatives of cholesterol. Preferred sterols include phytosterols, such as soya sterol.

Oils useful in forming antimicrobial oil-in-water emulsions of the present invention include a broad spectrum of water-immiscible materials, such as soybean oil, avocado oil, squalene oil, squalane oil, sesame oil, olive oil, canola oil, corn oil, rapeseed oil, safflower oil, sunflower oil, fish oils, flavor oils, water insoluble vitamins, and mixtures thereof.

In another embodiment of the invention, at least a portion of the oily discontinuous phase may be in the form of lipid structures including, but not limited to, unilamellar, multilamellar, and paucilamellar lipid vesicles, micelles, and lamellar phases.

The antimicrobial emulsions of the present invention can be used, for example, in pharmaceutical preparations (e.g., creams, solutions and suspensions) to inhibit the growth of a wide variety of infectious pathogens, including bacteria, viruses, and fungi. Accordingly, the present invention also provides an antimicrobial preparation suitable for pharmaceutical administration made up of an antimicrobial emulsion of the invention and a pharmaceutically acceptable carrier. The preparation can be applied topically to skin surface areas, mucus membranes, or oral surfaces, for example, as a cream, gel, spray, or mouthwash to treat or prevent bacterial infections such as *Propionibacterium acnes, Neisseria gonorrhea,* Streptococcus, and *Staphylococcus epidermidis.* Alternatively, the preparation can be administered internally, for example, to inactivate pathogenic microorganisms, such as *Helicobacter priori*. Accordingly, the present invention further provides a method for inhibiting the growth of an infectious pathogen by topical or oral administration of the antimicrobial emulsion of the invention.

DETAILED DESCRIPTION OF THE INVENTION

The present invention relates to a stable antimicrobial oil-in-water emulsion made of positively charged droplets of a lipid-containing oily discontinuous phase dispersed in an aqueous continuous phase.

The term "antimicrobial," as used herein, means having the ability to inactivate infectious pathogens. The term "inactivate", as used herein, includes but is not limited to, killing or inhibiting growth of the organism. The term "infectious pathogen", as used herein, includes, but is not limited to, fungi, viruses, bacteria, and parasites. The antimicrobial emulsion of the present invention inactivates a wide variety of infectious pathogens. It appears that inactivation is achieved by binding of the oil phase to negatively charged proteins contained in the biological membrane of the pathogen, and disrupting the membrane structure. Accordingly, one aspect of the present invention provides an antimicrobial oil-in-water emulsion which contains materials capable of binding to the membrane of a pathogen, such as a bacterium, a virus, or a fungus, and disrupting the membrane structure so that the pathogen is inactivated.

The term "emulsion," as used herein, includes both classic oil-in-water dispersions or droplets, as well as other lipid structures which can form as a result of hydrophobic forces which drive apolar residues (i.e., long hydrocarbon chains) away from water and drive polar head groups toward water, when a water immiscible oily phase is mixed with an aqueous phase. These other lipid structures include, but are not limited to, unilamellar, paucilamellar, and multilamellar lipid vesicles, micelles, and lamellar phases. These other lipid structures also contain an amphiphile selected from the group consisting of glycerol monooleate (GMO), glycerol trioleate (GTO), glycerol monolaurate (GML), and glycerol dilaurate (GDL) as the primary lipid and a dodacyl to hexadecyl cationic halogen-containing compound as a positive charge producing agent. These other lipid structures can also further include at least one sterol, preferably a phytosterol. In a preferred embodiment of the invention, GMO is used as the primary lipid. The term "primary lipid", refers to the lipid which constitutes the greatest proportion by weight of any single lipid contained in the oily discontinuous phase.

Antimicrobial oil-in-water emulsions of the present invention can be formed using classic emulsion forming techniques which are well known in the art. In brief, the lipid-oil phase is mixed with the aqueous phase under relatively high shear forces to obtain an oil-in-water emulsion containing oil droplets which are approximately 1 micron in diameter. More particularly, a positively charged lipid-containing oily discontinuous phase is formed by blending (a) an oil carrier; (b) an amphiphile selected from the group consisting of GMO, GTO, GML, or GDL; and (c) a cationic halogen-containing compound having a $C_{12}-C_{16}$ chain, along with any other compatible amphiphiles or emulsifiers, such as Polysorbate 60, and any sterols or other lipophilic materials to be incorporated into the lipid-oil phase.

Once the lipid-oil phase is formed, it is heated and blended with an aqueous phase (e.g., water, saline, or any other aqueous solution which can hydrate the lipids) on a volume to volume basis ranging from about 1:4 to 1:2, preferably about 1:3 lipidoil phase to aqueous phase. The lipid-oil and aqueous phases can be blended using any apparatus capable of producing the high shear mixing forces, including, for example, French Press, Novamix (IGI Inc., Buena N.J.) or syringe mixer, or, alternatively by hand using two syringes.

Antimicrobial oil-in-water emulsions of the present invention provide the advantage of being stable in the presence of heat, acid, or base. For example, as shown below in Example 4, emulsions of the invention are not significantly altered or broken down when boiled or exposed to 1 N Nitric acid or 1 N sodium hydroxide. This stability makes the emulsions suitable for pharmaceutical administration, even internal administration.

Antimicrobial oil-in-water emulsions of the present invention can be used to inactivate a variety of infectious pathogens upon contact. As described in the examples below, microbes which are inactivated by the present invention include a wide variety of bacteria and fungi. For example, the presently disclosed emulsions can be used for oropharyngeal application, as a spray or mouthwash, to inactivate or prevent infection secondary to *Streptococcus pneumoniae,* Group A beta-hemolytic Streptococcus, *Haemophilus influenzae,* and *Neisseria meningitidis*. The presently disclosed emulsions can also be administered orally to inactivate or prevent gastrointestinal infections (e.g., gastritis or peptic ulcer disease) secondary to *Helicobacter pylori*. The presently disclosed emulsions can also be used for veneral application, as a cream, gel, or suppository to inactivate or prevent infection secondary to *Neisseria gonorrhoeae, Gardnerella vaginalis,* and Group B Streptococcus. The presently disclosed emulsions can also be used for dermatological application as a cream or gel to inactivate or prevent infection secondary to *Propionibacterium acnes, Staphylococcus aureus, Staphylococcus epidermidis,* and Group B Streptococcus. In a preferred embodiment of the invention, antimicrobial emulsions of the present invention are used to prevent infection by gram positive bacteria.

The present invention also provides an antimicrobial preparation suitable for pharmaceutical administration consisting of the antimicrobial emulsion of the present invention and a pharmaceutically acceptable carrier. The term "pharmaceutically acceptable carrier," as used herein, refers to any physiologically compatible carrier for stabilizing emulsions of the present invention for pharmaceutical administrstion. Use of such media and agents for pharmaceutically active substances is well known in the art. Except insofar as any conventional media or agent is incompatible with the emulsions of the present invention, use thereof in a pharmaceutical preparation is contemplated.

The present invention further provides methods for inhibiting the growth of an infectious pathogen by topical, or systemic administration of the antimicrobial emulsion of the present invention, preferably in the form of a pharmaceutical preparation. The term "topical," as used herein, includes application to mucous membranes, oral surfaces, skin, inner ear surfaces, or the surfaces of any bodily orifice, such as the vagina or rectum. The term "systemic", as used herein, includes any form of internal administration, including but not limited to, oral and intravenous administration.

The following examples will illustrate the efficacy of the invention.

EXAMPLES

Example 1

In this Example, a series of lipid-containing oil-in-water emulsions having either GMO or GMS as the primary lipid and a charge producing agent were formed and characterized with regard to purity, pH and size of oil droplets.

In this Example, the antimicrobial oil-in-water emulsion is formed as follows: a lipid-oil phase containing approximately 21% by weight GMO, GTO, GML, or GDL, 0.8 to 0.9% by weight cationic halogen-containing compound having a $C_{12}$–$C_{16}$ chain, 67% by weight carrier oil such as soybean oil, 5% by weight Polysorbate 60 (Polyoxyethylene 20 sorbitan monostearate), and 6% by weight soya sterol is heated for approximately one hour at 86° C. The lipid-oil phase is then blended with an aqueous phase containing water at 65° C. using a 5 ml syringe machine on a volume to volume basis of 13 parts lipid-oil to 37 parts water.

Table 1 shows the amount of each chemical component used to form the lipidoil phase of emulsions having glycerol monooleate (GMO) or glycerol monostearate (GMS) as the primary lipids and cetylpyridinium chloride (CPC), cetylpyridinium bromide (CPB), cetyltrimethylammonium bromide (CTAB), or dimethyldioctadecylammonium bromide (DDDAB) as positive charge producing agents, and using oleic acid as a negative charge producing agent.

TABLE 1

|  | GMO/CPC | GMO/CPB | GMO/CTAB | GMS/DDDAB | GMO/OLEIC | GMS/CPC |
|---|---|---|---|---|---|---|
| GMO | 3.43 g | 3.43 g | 3.43 g | — | 3.43 g | — |
| GMS | — | — | — | 3.43 g | — | 3.43 g |
| Soya Sterol or cholesterol | 0.96 g | 0.96 g | 0.96 g | 0.96 g | 0.96 g | 0.96 g |
| Tween 60 | 0.84 g | 0.84 g | 0.84 g | 0.84 g | 0.84 g | 0.84 g |
| Soybean Oil | 11 g | 11 g | 11 g | 11 g | 11 g | 11 g |
| CPC | 130 mg | — | — | — | — | 130 mg |
| CPB | — | 150 mg | — | — | — | — |
| CTAB | — | — | 140 mg | — | — | — |
| DDDAB | — | — | — | 240 mg | — | — |
| Oleic Acid | — | — | — | — | 108 mg | — |

Table 2 shows the pH of the emulsions shown in Table 1. Also shown is the size of the lipid-oil droplets of the emulsions measured on a Coulter LS 130 Laser sizing instrument equipped with a circulating waterbath.

TABLE 2

| Chemical Components of Emulsions | Charge | pH | Mean Coulter Size in Microns | Mean Coulter Range in Microns |
|---|---|---|---|---|
| GMO/CPC | Positive | 3.72 | 1.049 | 0.720–1.401 |
| GMO/CPB | Positive | 4.31 | 0.891 | 0.680–1.124 |
| GMO/CTAB | Positive | 4.82 | 1.143 | 0.647–1.358 |
| GMS/DDDAB | Positive | 5.86 | 1.080 | 0.694–1.532 |
| GMO/Oleic acid | Negative | 4.45 | 1.078 | 0.738–1.448 |
| GMS/CPC | Positive | 3.72 | 1.047 | 0.677–1.497 |

Example 2

In this Example, the microbicidal activities of each of the emulsions described in Example 1 were compared. For this purpose, the ability of each of the emulsions to kill *Staphylococcus aureus* type 8 was tested as follows:

Bacteria were innoculated into liquid media (Trypticase soy broth or Schaedler's broth) and incubated at 37° C. for 1–7 hours. An optical density at a wavelength of 650 nm and a quantitative culture were then performed on each broth culture. One milliliter of each bacterial broth was then mixed with one milliliter of emulsion for 10 or 30 minutes. Quantitative cultures were then performed in duplicate on each mixture. Plates containing bacteria were incubated at 37° C. for 18 hours and then counted.

The percentage of bacteria killed was then determined by the following equation.

$$\% \text{ kill} = \frac{(A - B)}{A} \times 100$$

A=The total number of bacteria innoculated

B=The total number counted after mixing with an emulsion

Table 3 lists the percentages of Staphylococcus aureus type 8 killed by each emulsion or water after a 10 or 30 minute incubation with $2 \times 10^7$ bacteria.

TABLE 3

| Chemical Components of Preparation | % Inactivate After a 10 Minute Incubation | % Inactivate After a 30 Minute Incubation |
|---|---|---|
| GMO/CPC | 100 | 100 |
| GMO/CPB | 100 | 100 |
| GMO/CTAB | 99.99 | 99.99 |
| GMO/DDDAB | 65 | 0 |
| GMO/Oleic acid | 0 | 0 |
| GMS/CPC | 65 | 0 |
| Control alone | 50 | 0 |

From Table 3 one can see that the positively charged glycerol monooleate (GMO) emulsions inactivate *Staphylococcus aureus* type 8 while the positively charged glycerol monostearate (GMS/CPC) emulsion fails to inactivate. In addition, only the cationic compounds having a $C_{12}$–$C_{16}$ chain containing either chloride or bromide, i.e., CPC, CPB or CTAB, and not the dioctadecyl cationic compound (DDDAB) or oleic acid (having a negative charge), were associated with significant microbicidal activity. The inactivation of this bacterium, Staphylococcus aureus, is therefore more effective using GMO emulsions containing a chloride or bromide containing cationic compound having a $C_{12}$–$C_{16}$ chain.

Example 3

In this Example, the ability of the GMO/CPC emulsion formed in Example 1 to kill a variety of bacteria and yeast was tested.

The assay described above in Example 2 was used to measure the microbicidal activity of the GMO/CPC emulsion against a number of bacteria and fungi, except for the following changes:

Yeast were innoculated into Sabouraud's broth and incubated at 30° C. for 6 hours, mixed with the GMO/CPC emulsion for 10 or 30 minutes, plated and incubated at 37 C. for 18 hours before counting.

*P. acnes* was grown anaerobically in Schaedler's broth for 24 hours, mixed with emulsion for 10 or 30 minutes, plated on Trypticase soy agar plates with 5% sheep blood and incubated anaerobically for 72 hours prior to counting.

G. vaginalis was plated on Trypticase soy agar plates with 5% sheep blood and incubated in 5% $CO_2$ at 37° C. for 72 hours. Colonies were swabbed from plates and innoculated into Schaedler's broth at the density of a 0.5 McFarland standard. This broth/bacterial mixture was then incubated with the emulsion for 10 or 30 minutes and then plated on Trypticase soy agar plates with 5% sheep blood. Plates were incubated for 72 hours in 5% $CO_2$ at 37° C. before counting colonies.

Table 4 lists the percentage of gram positive bacteria killed after a 10 or 30 minute incubation of the GMO/CPC emulsion with between 105 and 108 bacteria. The listed bacteria can generally be categorized as follows: (a) those which colonize on the skin which include *Staphylococcus aureus* (type 8), *Staphylococcus aureus* (type 5), *Staphylococcus epidermidis* (strain 977), Group B Streptococcus (capsular type III), Group A Streptococcus (beta-hemolytic), and *Propionibacterium acneus;* (b) those which colonize in the oropharynx which include Group A Streptococcus (beta-hemolytic), *Streptococcus pneumoniae* (type 5), and *Streptococcus mutans;* and (c) those which colonize or infect the vagina which include *Gardnerella vaginalis* and Group B Streptococcus (capsular type III).

TABLE 4

| Gram Positive Bacteria | Innoculum (CFU)• | % Inactive after a 10 Minute Incubation | % Inactive after a 30 Minute Incubation |
|---|---|---|---|
| *Staphylococcus aureus* (type 8/bactermic isolate) | $2 \times 10^7$ | 99.99 | 99.99 |
| *Staphylococcus aureus* (type 5 bacteremic isolate) | $9 \times 10^6$ | 100 | 99.99 |
| *Staphylococcus epidermidis* (strain 97) | $8 \times 10^5$ | 100 | 100 |
| Group B *Streptococcus* (capsular type III - neonatal sepsis isolate) | $2.9 \times 10^7$ $2.9 \times 10^7$ | 99.99 99.99 | 100 100 |
| Group A beta-hemolytic (type 1) *Streptococcus* (ATCC 12344) | $3.3 \times 10^7$ | 99.99 | 99.99 |
| *Listeria monocytogenes* (type 2) (ATCC 19112) | $1.3 \times 10^8$ | 99.99 | 99.99 |
| *Streptococcis pneumoniae* (type 5) (ATCC 6305) | $6.4 \times 10^7$ | 100 | 100 |
| Streptococcus mutans (ATCC 25179) | $6.5 \times 10^6$ | 96.2 | 96.8 |
| Propionibacterium acnes (ATCC 6919) | $1.2 \times 10^8$ | 100 | 100 |
| Enterococcus fecalis (ATCC 19433) | $3.7 \times 10^7$ | 99.36 | 99.98 |
| Gardnerella vaginalis (ATCC 14018) | $5.5 \times 10^7$ | 100 | 100 |
| Lactobacillus acidophilus (ATCC 4356) | $5.0 \times 10^5$ | 100 | 100 |

•CFU '2 colony forming units

Table 5 demonstrates that all gram positive bacteria which cause significant human clinical infections were exquisitely sensitive to the microbicidal action of the GMO/CPC emulsion.

Table 6 shows the percentage of gram negative bacteria killed after a 10 or 30 minute incubation of the GMO/CPC emulsion with between $10^5$ and $10^8$ bacteria. Included in the table are gram negative bacteria which colonize in the oropharynx, such as *Haemophilus infiuenzae* (capsular type b) and *Neisseria meningitidis* type b; the gastrointestinal tract, such as *Helicobacter pylori;* and the vagina, such as *Neisseria gonorrhoeae*.

TABLE 5

| Gram Negative Bacteria | Innoculum (CFU)• | % Inactive after a 10 Minute Incubation | % Inactive after a 30 Minute Incubation |
|---|---|---|---|
| *Escherichia coli* type O18:K1 | $2.1 \times 10^7$ | 97.1 | 96.7 |
| *Escherichia coli* type O18:K– | $3.2 \times 10^7$ | 89.7 | 99.6 |
| *Escherichia coli* J5 (epimerase deficient) | $3 \times 10^7$ | 94 | 85 |
| *Flavobacterium menengosepticum* Group A (ATCC 13253) | $2.1 \times 10^6$ | 0 | 47.6 |
| *Klebsiella pneumonia* type O12K+ | $5 \times 10^7$ | 98.3 | 99.9 |
| *Pseudomonas aeruginosa* type FD-1 | $3.8 \times 10^7$ | 99 | 99 |
| *Pseudomonas aeruginosa* MEP strain 2192 | $8 \times 10^6$ | 99.1 | 97.5 |
| *Haemophilus influenzae* capsular type b (ATCVC 33533) | $1 \times 10^7$ | 99.99 | 99.99 |
| *Neisseria meningitidis* (ATCC 13090) | $1.6 \times 10^8$ | 100 | 100 |
| *Neisseria gonorrhoeae* (ATCC 9793) | $1.2 \times 10^6$ | 100 | 100 |
| *Helicobacter pulori* (ATCC 43504) | $3 \times 10^6$ | 100 | 100 |
| *Helicobacter pylori* (ATCC 43629) | $4.7 \times 10^6$ | 100 | 100 |
| *Helicobacter pylori* (ATCC 49503) | $2 \times 10^6$ | 100 | 100 |
| *Helicobacter pylori* (ATCC 43579) | $7 \times 10^6$ | 100 | 100 |

Table 5 illustrates that at 30 minutes there is inactivation of at least 85% of the innoculum of all gram negative bacteria tested except for *Flavobacterium meningosepticum*. The encapsulated type b *Haemophilus infiuenzae,* type b *Neisseria meningitidis, Neisseria gonorrhoeae,* and *Helicobacter pylori* bacteria, which have relatively rough LPS types compared to the other gram negative bacteria, are exquisitely sensitive to the microbicidal activity of the GMO/CPC emulsion.

Table 6 shows the percentage of the two Candida species listed in Table 9 killed after a 10 or 30 minute incubation of the GMO/CPC emulsion with $10^5$ yeast.

TABLE 6

| Yeast | Innoculum (CFU) | % Inactive After a 10 Minute Incubation | % Inactive After a 30 Minute Incubation |
|---|---|---|---|
| *Candida albicans* (clinical blood isolate) | $3.2 \times 10^5$ | 62.5 | 62.5 |
| *Candida tropicalis* (clinical blood isolate) | $5.4 \times 10^5$ | 100 | 100 |

Table 6 demonstrates that significant inactivating of the *Candida albicans* species occurs after only a 10–30 minute incubation with the GMO/CPC emulsion.

Example 4

In this Example, GMO emulsions containing different concentrations of CPC were tested for antimicrobicidal activity against *Staphylococcus aureus* type 8. Table 7 shows percentages of *Staphylococcus aureus* type 8 killed after a 10 or 30 minute incubation of the GMO emulsions with $10^7$ bacteria.

TABLE 7

| Chemical Components of Emulsion | Initial Innocculum of *Staphylococcus Aureus* Type 8 | % Inactive After a 10 Minute Incubation | % Inactive After a 30 Minute Incubation |
|---|---|---|---|
| GMO/CPC $C_{21}H_{38}NCl$ | 10,000,000 CFU [1.8 mg/ml emulsion] | 100 | 100 |
| GMO/CPC $C_{21}H_{38}NCl$ | 10,000,000 CFU [0.9 mg/ml emulsion] | 99.5 | 100 |
| GMO/CPC $C_{21}H_{38}NCl$ | 10,000,000 CFU [0.45 mg/ml emulsion] | 54 | 99.5 |
| GMO/CPC $C_{21}H_{38}NCl$ | 10,000,000 CFU [0.23 mg/ml emulsion | 39 | 32 |
| GMO/CPC $C_{21}H_{38}NCl$ | 10,000,000 CFU [0.028 mg/ml emulsion] | 0 | 0 |
| GMO | 10,000,000 CFU | 0 | 0 |
| GMO/Oleic acid $C_{18}H_{34}O_2$ | 10,000,000 CFU | 0 | 0 |
| Water alone | 10,000,000 CFU | 10 | 0 |

Table 7 demonstrates that Staphylococcus aureus type 8 bacteria were sensitive to the microbicidal action of the GMO/CPC emulsion at CPC concentrations of greater than 0.23 mg/ml of emulsion.

Example 5

In this Example, the GMO/CPC emulsion formed in Example 1 was tested for stability in the presence of heat, acid and base. Table 9 shows the effect of boiling for one hour on breakdown or aggregation of the GMO/CPC emulsion, shows the effects of mixing equal volumes of 1 N Nitric acid and GMO/CPC emulsion for two hours on breakdown or aggregation of the GMO/CPC emulsion, and the effects of mixing equal volumes of 1 N Sodium hydroxide and GMO/CPC emulsion for two hours on breakdown or aggregation of the GMO/CPC emulsion.

TABLE 8

| Chemical Components of Emulsion | Intervention | Mean Coulter Size in Microns | Mean Coulter Range in Microns |
|---|---|---|---|
| GMO/CPC | No boiling | 1.008 | 0.720–1.337 |
| GMO/CPC | Boiling 1 hour | 1.167 | 0.654–1.517 |
| GMO/CPC | No acid treatment | 1.008 | 0.720–1.337 |
| GMO/CPC | 1N $HNO_3$ for 2 hours | 1.062 | 0.675–1.569 |
| GMO/CPC | No base treatment | 1.008 | 0.720–1.337 |
| GMO/CPC | 1N NaOH for 2 hours | 0.804 | 0.658–0.969 |

Table 8 shows that: (a) boiling for 1 hour does not significantly alter the breakdown or size of the emulsion; (b) 1 N Nitric acid exposure for 2 hours does not significantly alter the size or aggregate profile of the CMO/CPC emulsion; and (c) 1 N Sodium hydroxide exposure for 2 hours causes a 20% decrease in the mean size of the emulsion without disrupting the emulsion or causing aggregation.

From the above-described Examples 1–4, it is evident that the antimicrobial oil-in-water emulsions of the present invention have significant microbicidal activity against a wide variety of bacteria and yeast, even at extremely low concentrations of cationic halogen-containing compound, such as CPC. Furthermore, the emulsions of the invention are stable in the presence of heat, acid, and base, making them very suitable for pharmaceutical administration, whether topical, oral or systemic.

Those skilled in the art will recognize, or be able to ascertain using no more than routine experimentation, many equivalents to the specific embodiments of the invention described herein. Such equivalents are intended to be encompassed by the following claims.

What is claimed is:

1. A method of inhibiting the growth of an infectious pathogen comprising the step of topical application of an antimicrobial oil-in-water emulsion, said antimicrobial emulsion being in the form of positively charged droplets of a lipid-containing oily discontinuous phase dispersed in a continuous aqueous phase, the oily discontinuous phase consisting essentially of:

a. an oil;
   b. glycerol monooleate as the primary lipid; and
   c. a cationic halogen-containing compound having a $C_{12}$–$C_{16}$ chain selected from the group consisting of cetylpyridinium chloride, cetylpyridinium bromide, cetyltrimethylammonium bromide, cetyltrimethylammonium chloride, cetyldimethylethylammonium bromide, cetylbenzyldimethylammonium chloride, cetyltributylphosphonium bromide, dodecyltrimethylammonium bromide, and tetradecyltrimethylammonium bromide.

2. The method of claim 1, wherein the oil is selected from the group consisting of soybean oil, squalene oil, sesame oil, olive oil, canola oil, corn oil, rapeseed oil, safflower oil, sunflower oil, fish oils, avocado oil, flavor oils, water insoluble vitamins, and mixtures thereof.

3. The method of claim 1, wherein said topical application comprises oral application.

4. The method of claim 1, wherein said topical application comprises application to a mucous membrane via inhalation.

5. The method of claim 1, wherein said topical application comprises vaginal application.

6. The method of claim 1, wherein at least a portion of the oily discontinuous phase is in the form of a lipid structure selected from the group consisting of unilamellar, multilamellar, and paucilamellar lipid vesicles, micelles, and lamellar phases.

7. A method of inhibiting the growth of an infectious pathogen comprising the step of topical application of an antimicrobial oil-in-water emulsion, said antimicrobial emulsion being in the form of positively charged droplets of a lipid-containing oily discontinuous phase dispersed in a continuous aqueous phase, the oily discontinuous phase consisting essentially of:

a. an oil selected from the group consisting of soybean oil, squalene oil, sesame oil, olive oil, canola oil, corn oil, rapeseed oil, safflower oil, sunflower oil, fish oils, avocado oil, flavor oils, water insoluble vitamins, and mixtures thereof;
   b. glycerol monooleate; and
   c. a cationic halogen-containing compound having a $C_{12}$–$C_{16}$ chain selected from the group consisting of cetylpyridinium chloride, cetylpyridinium bromide, and cetyltrimethylammonium bromide.

8. A method of internally inhibiting the growth of an infectious pathogen in a subject comprising the step of systemically administering to the subject an antimicrobial oil-in-water emulsion, said antimicrobial emulsion being in the form of positively charged droplets of a lipid-containing oily discontinuous phase dispersed in a continuous aqueous phase, the oily discontinuous phase consisting essentially of:

a. an oil;
b. glycerol monooleate as the primary lipid; and
c. a cationic halogen-containing compound having a $C_{12}$–$C_{16}$ chain selected from the group consisting of cetylpyridinium chloride, cetylpyridinium bromide, and cetyltrimethylammonium bromide.

9. The method of claim 8 wherein said step of systemically administering comprises enteral administration.

10. A method of inhibiting the growth of an infectious pathogen comprising the step of topical application of an antimicrobial oil-in-water emulsion, said antimicrobial emulsion being in the form of positively charged droplets of a lipid-containing oily discontinuous phase dispersed in a continuous aqueous phase, the oily discontinuous phase consisting essentially of:

a. an oil;
b. glycerol monooleate;
c. a cationic halogen-containing compound having a $C_{12}$–$C_{16}$ chain selected from the group consisting of cetylpyridinium chloride, cetylpyridinium bromide, cetyltrimethylammonium bromide, cetyltrimethylammonium chloride, cetyldimethylethylammonium bromide, cetylbenzyldimethylammonium chloride, cetyltributylphosphonium bromide, dodecyltrimethylammonium bromide, and tetradecyltrimethylammonium bromide; and
d. at least one sterol selected from the group consisting of cholesterol, cholesterol derivatives, hydrocortisone, phytosterol, and mixtures thereof.

11. The method of claim 10, wherein said oil is selected from the group consisting of soybean oil, squalene oil, sesame oil, olive oil, canola oil, corn oil, rapeseed oil, safflower oil, sunflower oil, fish oils, avocado oil, flavor oils, water insoluble vitamins, and mixtures thereof, and wherein said cationic halogen-containing compound having a $C_{12}$–$C_{16}$ chain is selected from the group consisting of cetylpyridinium chloride, cetylpyridinium bromide, and cetyltrimethylammonium bromide.

\* \* \* \* \*

UNITED STATES PATENT AND TRADEMARK OFFICE
CERTIFICATE OF CORRECTION

PATENT NO. : 5,549,901
DATED : August 27, 1996
INVENTOR(S) : D. Craig Wright

It is certified that error appears in the above-indentified patent and that said Letters Patent is hereby corrected as shown below:

Column 3, line 2, replace "Helicobacter priori" with --Helicobacter Pylori--.

Column 7, line 13, replace "between 105 and 108" with --between $10^5$ and $10^8$ .

Column 7, line 57, replace "•CFU '2 colony forming units" with --•CFU= colony forming units-- .

Column 8, line 25, replace "Neisseria meningitidis (ATCC" with --Neisseria meningitidis type b (ATCC--.

Column 8, line 28, replace "Helicobacter pulori" with -- Helicobacter pylori--.

Signed and Sealed this

Thirteenth Day of May, 1997

Attest:

Attesting Officer

BRUCE LEHMAN

Commissioner of Patents and Trademarks